United States Patent [19]

Rayman

[11] Patent Number: 5,004,584

[45] Date of Patent: Apr. 2, 1991

[54] DEVICE FOR TESTING FLUIDS

[76] Inventor: Gerard A. Rayman, 10 Sternes Way, Stapleford, Cambridge, United Kingdom

[21] Appl. No.: 210,228

[22] Filed: Jun. 23, 1988

[30] Foreign Application Priority Data

Jun. 26, 1987 [GB] United Kingdom ............... 8714979
Mar. 8, 1988 [GB] United Kingdom ............... 8805431

[51] Int. Cl.⁵ ............................................. G01N 31/22
[52] U.S. Cl. ........................................ 422/58; 422/56; 422/57; 422/61; 422/102; 436/66; 436/164; 436/169
[58] Field of Search .................... 422/58, 57, 61, 102, 422/104, 56; 436/66, 164, 169; 204/402, 409, 415, 418

[56] References Cited

U.S. PATENT DOCUMENTS

| 4,135,884 | 1/1979 | Shen ..................................... 422/58 |
| 4,260,392 | 4/1981 | Lee . |
| 4,298,688 | 11/1981 | Kallies .................................. 422/58 |
| 4,302,313 | 11/1981 | Columbus ........................... 204/409 |
| 4,308,028 | 12/1981 | Elkins .................................. 422/58 |
| 4,378,344 | 3/1983 | Zahradnik et al. ................. 422/58 |
| 4,582,684 | 4/1986 | Vogel et al. . |
| 4,654,127 | 3/1987 | Baker et al. ........................ 422/68 |
| 4,661,319 | 4/1987 | Lape .................................... 422/68 |
| 4,678,757 | 7/1987 | Rapkin et al. ...................... 422/57 |
| 4,761,381 | 8/1988 | Blatt et al. ......................... 422/102 |
| 4,797,256 | 1/1989 | Watlington, IV ................. 422/104 |

FOREIGN PATENT DOCUMENTS

| 0073513 | 8/1982 | European Pat. Off. . |
| 136362 | 3/1984 | European Pat. Off. . |
| 138152 | 10/1984 | European Pat. Off. . |
| 171148 | 6/1985 | European Pat. Off. . |
| 213728 | 7/1986 | European Pat. Off. . |
| 2711201 | 9/1978 | Fed. Rep. of Germany . |
| 2007838 | 11/1978 | United Kingdom . |
| 2090659 | 7/1982 | United Kingdom . |
| 86/00138 | 1/1986 | World Int. Prop. O. . |

OTHER PUBLICATIONS

German Search Report (1 page).
EPC Search Report (2 pages).

Primary Examiner—Robert J. Warden
Assistant Examiner—Jill Johnston
Attorney, Agent, or Firm—Rogers, Howell & Haferkamp

[57] ABSTRACT

Blood tests are made using a diagnostic stick which has a testing chamber at one end of the stick. The chamber has an open end and is dimensioned so that blood can be drawn in to fill the chamber by capillary action. A testing surface is either mounted in the chamber or is on a separate probe which can be immersed in blood in the chamber. The invention can be used with fluids other than blood.

10 Claims, 2 Drawing Sheets

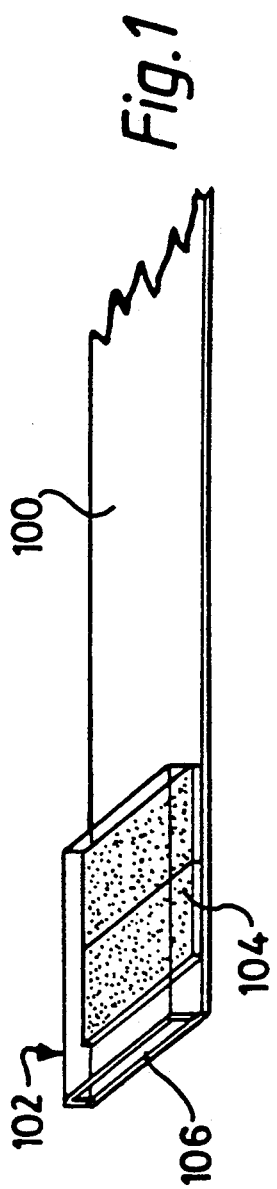
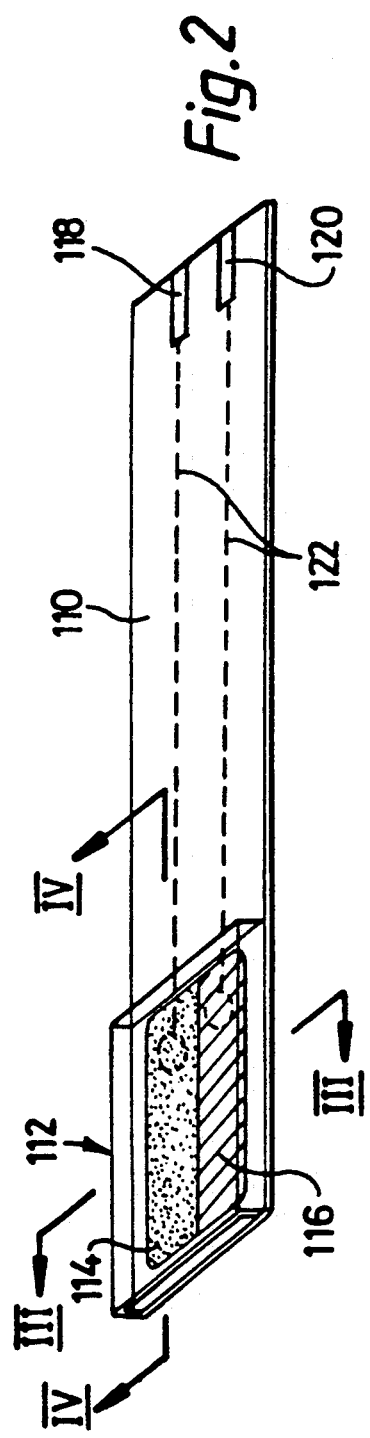
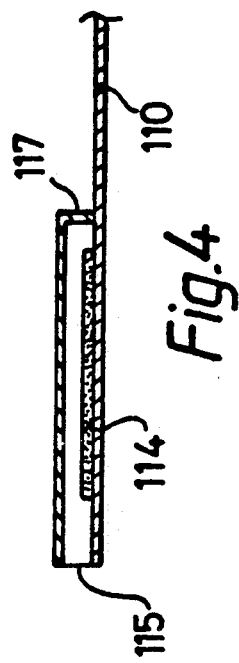
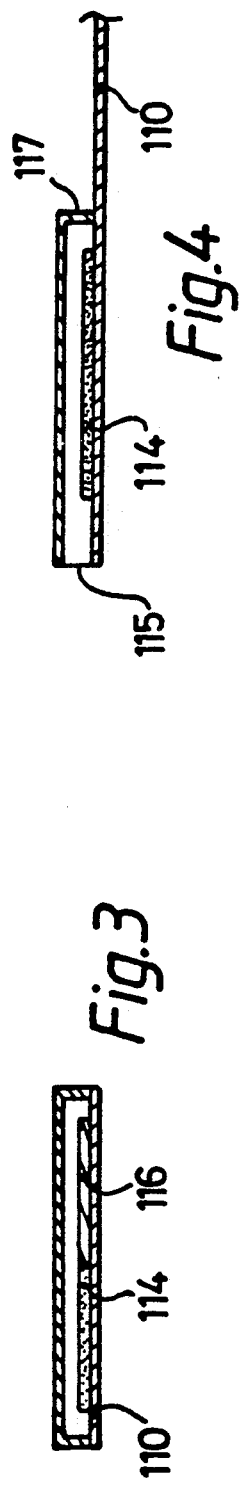

DEVICE FOR TESTING FLUIDS

This invention relates to a device for testing fluids. The device is particularly useful for testing body fluids, especially blood, and it allows blood testing to be carried out simply, quickly, and hygienically.

Certain blood tests are conventionally carried out using a diagnostic stick which carries a testing surface having a culture medium or chemical reagent on it. Sticks with an electrochemical testing surface are also known. Blood to be tested is brought into contact with the testing surface and it is important that precise coverage of the testing surface is achieved, i.e. that the whole of the surface is evenly brought into contact with the blood to be tested.

According to the present invention, there is provided a fluid testing device which has a chamber having an opening at one end, the chamber being adapted to be filled through capillary action when the opening is placed in a fluid, and a testing surface associated with the chamber and adapted to react to fluid in the chamber to produce an indication of properties of the fluid.

In a preferred form, the device is for testing blood, and in the rest of this specification, blood will be referred to as the fluid.

The testing surface may for example be a pair of pads which between them show an electrochemical effect when covered with blood, or a culture medium or other chemical reagent which produces a chemical reaction with the blood.

In the case of an electrochemical test, the device will also include electrical connections between the testing surfaces and terminals for connection to a read out device in a known manner. If the testing surface is a chemical reagent, then it will generally need to be wiped before a test result can be established In order for wiping to take place, the testing surface must be removed from the chamber, and this can be done in one of two ways. Either the chamber walls can be of flimsy construction so that the walls are themselves wiped away when the stick is drawn through, for example, a pad of cotton wool. This could be accomplished by making the walls of cellophane or a similar thin cellulose sheet. Alternatively, the testing surface may be mounted on a component of the device which can be placed in the capillary chamber and can be removed from the chamber after having been exposed to the blood in the chamber. On removal, the testing surfaces can be pulled past a surface which carries out a wiping action.

The end of the chamber opposite to the end with the opening may be substantially closed. However where the testing surface is on a separate stick or probe, the top end of the chamber may be open to allow the stick and the testing surface to be withdrawn. In the latter case, the wiping may be carried out by a doctor blade which scrapes blood off the testing surfaces, or by a body of absorbent material through which the stick and its testing surface has to pass.

The internal chamber walls are made from material which is wetted by the blood, in order to allow capillary action to occur. A suitable material for the chamber walls is cellulose.

It is preferred that the whole device be a one-time use device which can be supplied in a sealed, sterile package and can be discarded after use. It is advantageous when the blood sample on which the test is carried out is retained captive within the capillary chamber and can be discarded without the risk of any cross contamination of other patients if one blood sample should be infected.

In accordance with a second aspect the testing device is a two part testing device which comprises a sleeve and a testing stick, the stick being adapted to fit within the sleeve and carrying a fluid testing surface, and the sleeve having a capillary chamber adapted to be filled by capillary action when the tip of the sleeve is immersed in a source of fluid and into which the fluid testing surface of the stick can be dipped, and a second region, separate from the first region, and arranged to remove fluid from the fluid testing surface of the stick as the stick is drawn through.

Between the first region and second region, there is preferably a third region which accommodates the fluid testing surface of the stick. In practice, the device will be supplied with the fluid testing surface located in the third region mentioned above. Once a source of fluid is prepared, the tip of the sleeve at the end of the first region is introduced into the fluid which is then sucked up into the first region by capillary action, until the first region is full. At this point no further fluid can be sucked up. The stick is then pushed into the first region so that the fluid testing surface is in intimate contact over its whole area with the fluid in the first region. The stick remains there for a predetermined time and is then withdrawn from the sleeve past the second region where excess fluid is wiped off. The stick with its fluid testing surface is then removed and transferred to a separate environment where the testing process can be completed. Once the stick has been withdrawn, the sleeve will be discarded and the fluid used in the test will be trapped within the sleeve thus avoiding any mess.

Although the device is described here in relation to the testing of blood, it could equally well be applied to other fluids which require similar test procedures in conjunction with a testing surface, and the invention therefore also applies to a fluid testing device having any feature or combination of the features set forth above.

The invention will now be further described, by way of example, with reference to the accompanying drawings in which:

FIG. 1 shows a first embodiment of a blood testing device according to the invention;

FIG. 2 shows a second embodiment of blood testing device according to the invention;

FIGS. 3 and 4 are cross sectional views on the lines III—III and IV—IV respectively from FIG. 2;

Figure 5:
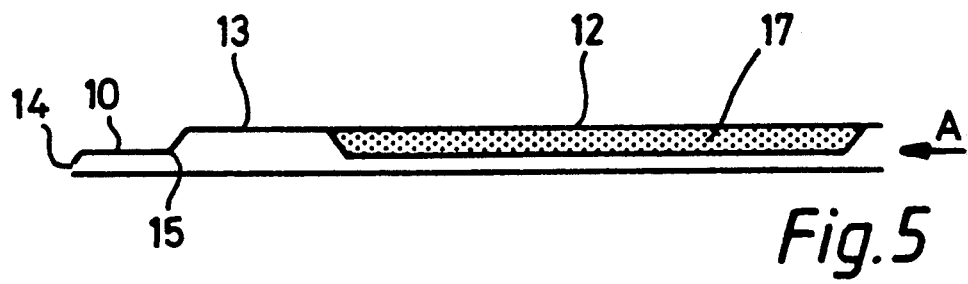
FIGS. 5, 6 and 7 show a third embodiment of a blood testing device according to the invention, in cross section and in three sequential stages of operation.

The device shown in FIG. 1 comprises a testing stick 100, the right hand end of which forms a handle by which the stick can be gripped and the left hand end of which carries a chamber 102 which is closed on all but one side and which encloses a testing surface 104 in the form of a chemical reagent. The extreme end 106 of the chamber 102 is open, and the internal dimensions of the chamber are such that when the open end 106 is dipped into blood, the blood is sucked up into the chamber by capilliary action until the chamber is full. The walls of the chamber are transparent so that the progress of the blood into the chamber can be watched by the operator and when the chamber is full then complete coverage of the reagent surface 104 is guaranteed. In accordance with a known procedure which varies in accordance with the nature of the reagent, the stick is then left in this condition for a predetermined time which may for example be 30 seconds The stick is then wiped to remove free blood from the surface 104, and the stick is then left for a further predetermined time which may again be 30 seconds before being examined to provide a test result.

In order to allow this to be done in a simple manner, the upstanding walls of the chamber 102 which lie above the plane of the strip 100 may be very thin and easily rupturable so that when the end of the strip is drawn through a pad of cotton wool, the walls are ruptured and pulled away from the strip at the same time as the blood is wiped off the reagent surface.

FIG. 2 shows an alternative testing device with a stick 110 and a chamber 112 with an open end and containing a testing surface made up of two different pad areas 114 and 116. The composition of these two areas is chosen such that when they are both immersed in blood a potential difference is established between them, the value of which depends on the properties of the blood.

This potential difference can be measured by inserting the opposite end of the stick in a testing machine which has terminals which make electrical contact with two terminals 118, 120 on the end of the stick 110. The terminals 118 and 120 are connected to the two reagent areas 114 and 116 by conductors 122.

For this type of testing, it is not necessary to remove the blood. Once the chamber 112 is full, it can remain full until the test has been completed and the stick is then thrown away.

The construction of the chamber 112 is illustrated in the sectional views of FIGS. 3 and 4 which show the open end 115 of the chamber and the other closed walls. It may be necessary to provide an opening in the top chamber wall 117 to allow the escape of air ahead of the entering blood.

In practice, the height of the chamber 112 will be constant throughout, i.e. the top face of the chamber will be a constant distance from the plane of the stick 110.

FIGS. 5 to 9 show two-part devices where a sleeve forms the capillary chamber, and a separate probe or stick which is inserted in the sleeve carries the testing surfaces.

Figure 6:
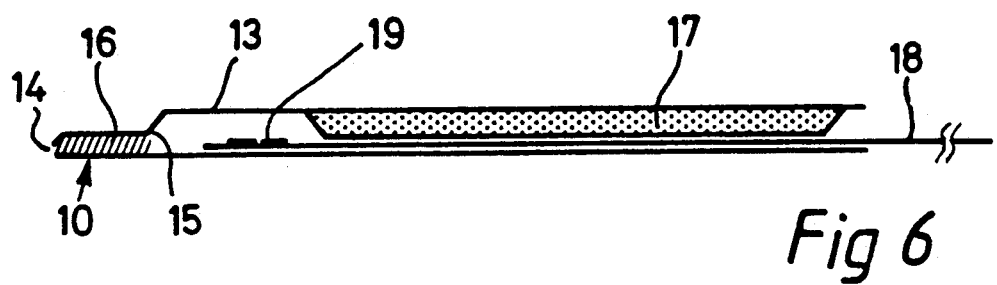
Figure 7:
Figure 8:
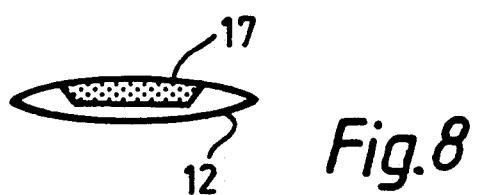
FIG. 8 shows a transverse cross section of the testing device shown in FIGS. 5 to 7.

FIG. 5 shows the sleeve alone of this device, and FIG. 8 is an end view of the sleeve taken in the direction of the arrow A from FIG. 5. As can be seen from FIG. 8, the sleeve can be in the form of a squashed cylinder. The sleeve has a first region 10, a second region 12 and a third region 13 which separates the regions 10 and 12. The region 10 is relatively narrow and has a mouth 14 of small dimensions. This first region 10 is constructed so that when the mouth 14 is dipped into a source of blood, the blood is drawn up into the region by capillary action. At its other end, the region 10 is bounded by a sharp transition 15 between the first region and the second region, and beyond this region the cross sectional area of the sleeve changes so that capillary action will not draw up any more blood than is necessary to completely fill the region 10. FIG. 6 illustrates this region completely filled with blood 16.

In the second region 12 a body of absorbent material 17 is provided. This absorbent material almost fills the cross section of the tube, as can be seen in FIG. 8.

The other part of the device is a testing or diagnostic stick 18 which has one or more blood testing surfaces 19 on which a chemical reagent has been laid down. When the device is ready for use, the stick 18 is in the position shown in FIG. 6, with the surfaces 19 in the third region 13. The stick will normally be held in this position by the friction between the shaft of the stick and the absorbent pad 17.

Once the first region 10 has been filled with blood as shown in FIG. 6, the test can begin. The stick 18 is pushed forward until the testing surfaces 19 are fully immersed in blood in the first region 10. The stick may be left in this position for a predetermined time, or immediately withdrawn depending on the test procedures adopted The whole of the blood testing surface is thus in intimate contact with blood so that an even application occurs.

The stick is then withdrawn, back to the position shown in FIG. 6 and may be held there for a predetermined length of time, or may be immediately withdrawn from the sleeve. When the stick is withdrawn, the blood testing surfaces 19 are wiped clean by the absorbent pad 17, and the surface blood is absorbed by the pad. By the time the surfaces are fully withdrawn from the sleeve, they have been thoroughly wiped of any trace of free blood. The stick with the testing surfaces 19 can then be taken to a separate area where the remainder of the test is carried out.

Figure 9:
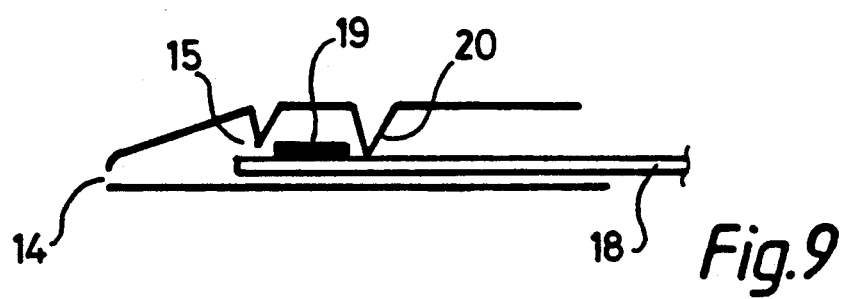
FIG. 9 shows part of a fourth embodiment of testing device in accordance with the invention.

In place of the absorbent pad 17, FIG. 9 shows a slightly different arrangement where the sleeve is formed with an inwardly extending rib 20 which forms a doctor blade which scrapes excess blood off the testing surfaces 19 as they are withdrawn.

It will be clear that the blood 16 which is drawn into the device remains trapped within the device and can be discarded with the sleeve once the stick 18 has been withdrawn.

For use in a conventional blood testing technique, the volume of the first region 10 can conveniently be in the region of 0.025 to 0.04 ml, and this will be sufficient blood to enable a test to be carried out. The cross sectional shape of the first region 10 must be sufficiently small to enable capillary action to take place. The wall can be inclined as shown in FIG. 9, provided that a meniscus fills the whole of the cross section.

In addition to the pad 17 shown in the drawings, there may be an auxiliary pad on the opposite side of the sleeve to remove any blood which adheres to the underside of the stick, as this is withdrawn from the sleeve. The sleeve is preferably of flexible material, so that the walls of the sleeve can be squeezed externally by finger pressure as the pad is drawn through, to exert some wiping pressure upon the pad 17.

This device therefore provides a simple, clean and accurate way of carrying out this type of blood test. An accurate test can be carried out using a minimum volume of blood which is automatically drawn into the sleeve. The blood is discarded with the sleeve after use, thus avoiding any mess and the construction of the sleeve ensures that the required process conditions are properly carried out.

Although the foregoing description refers mainly to blood testing, the invention can equally be applied to testing of other body fluids or indeed other fluids generally.

I claim:

1. A device for testing a fluid by a reaction of a component of the fluid with a regeant carried by a test probe, the device comprising:
   a sleeve member having a first and second end;
   a first chamber formed at the first end of the sleeve member, the chamber being adapted to be filled with the fluid by capillary action when the first end of the sleeve member is immersed in a source of the fluid;
   a probe member adapted to be inserted into the sleeve member and axially movably received in the sleeve member;
   a fluid testing surface on the probe member, the fluid testing surface being adapted to be inserted into the first chamber to react with the fluid in the first chamber; and
   a second chamber formed in the sleeve member, the second chamber being separate from the first chamber and being adapted to remove fluid from the fluid testing surface on the probe member as the probe member is moved axially through the second chamber.

2. The device as claimed in claim 1, wherein:
   the sleeve member is formed as a hollow tubular member with the first chamber at an end of the tubular member.

3. The device as claimed in claim 1, wherein:
   the fluid tested by the device is blood.

4. The device as claimed in claim 1, wherein:
   the first chamber includes at least one translucent wall enabling viewing a level of fluid in the first chamber.

5. The device as claimed in claim 1, wherein:
   the first chamber has internal walls constructed from a material that is wetted by the fluid.

6. The device as claimed in claim 5, wherein:
   the internal walls are constructed from cellulose.

7. The device as claimed in claim 5, wherein:
   the internal walls are constructed from cellophane.

8. The device as claimed in claim 1, wherein:
   the internal walls are constructed from a thin cellulose sheet.

9. The device as claimed in claim 1, wherein:
   the first chamber has first and second ends with the first end of the first chamber being substantially closed and the fluid testing surface of the probe member being inserted into the first chamber through the second end of the first chamber.

10. The device as claimed in claim 1, wherein:
    a third chamber is formed in the sleeve member between the first chamber and the second chamber, the third chamber being adapted to receive the fluid testing surface of the probe member prior to and after its insertion into the first chamber by axial movement of the probe member.

* * * * *